United States Patent [19]
Feldman et al.

[11] 4,201,218
[45] May 6, 1980

[54] THERAPEUTIC HEAT APPLICATION

[76] Inventors: Henry L. Feldman, 8844 Town & Country Blvd., Ellicott City, Md. 21043; Philip G. Berman, 11517 Karen Dr., Potomac, Md. 20854; William L. Washburn, 7704 Jansen Dr., Springfield, Va. 22152

[21] Appl. No.: 972,346

[22] Filed: Dec. 22, 1978

[51] Int. Cl.² .............................. A61F 7/00; H05B 3/06
[52] U.S. Cl. .................................... 128/402; 128/798; 219/211; 219/313; 219/523; 219/527; 219/528
[58] Field of Search ............... 219/211, 212, 313, 316, 219/523, 527, 528, 535, 549; 128/236, 260, 399, 400, 402, 403, 404

[56] References Cited

U.S. PATENT DOCUMENTS

| | | | |
|---|---|---|---|
| 2,178,397 | 10/1939 | Larkey | 219/313 |
| 3,016,446 | 1/1962 | Kalbach | 219/528 |
| 3,178,559 | 4/1965 | Fogel et al. | 219/527 |
| 3,195,539 | 7/1965 | Hyman | 128/236 |
| 3,292,628 | 12/1966 | Maxwell et al. | 128/402 |
| 3,298,368 | 1/1967 | Charos | 128/260 |
| 3,465,120 | 9/1969 | Merna | 219/211 |
| 3,470,350 | 9/1969 | Lewis | 219/211 |
| 3,569,666 | 3/1971 | Murphy et al. | 219/211 |
| 3,955,063 | 5/1976 | Berger | 219/527 X |

FOREIGN PATENT DOCUMENTS

109776  9/1966  Norway .................................... 219/527

*Primary Examiner*—Volodymyr Y. Mayewsky

[57] ABSTRACT

A portable heating device includes an envelope made by heat-sealing the edges of two flexible polymeric films, and a heat source within the envelope including, in one embodiment, a ribbon of conductive resistance heating element material folded into a generally sinuous, flat pattern within the envelope, and a nonconductive liquid such as silicone oil in the envelope and surrounding the heating element. In a second embodiment, the heat source is a semiconductor device. The envelope is carried by a strap or the like to hold the envelope next to a selected portion of the body for localized heating thereof. The heating element in the first embodiment is electrically connected to a power source such as batteries, and, in the second embodiment, the semiconductor device is connected to a control circuit which is connected to batteries.

5 Claims, 10 Drawing Figures

THERAPEUTIC HEAT APPLICATION

This invention relates to an improved therapeutic device and particularly to an improved device for applying heat to injured body areas.

BACKGROUND OF THE INVENTION

It has long been recognized that the application of heat to muscles or joints which have been strained or injured or which suffer from certain ailments is highly beneficial and comforting. Sports related strains or injuries, in either human or other animal participants, have received particular attention. While the application of cold packs is often used immediately following an injury for an interval of some hours, subsequent treatment is often by applying heat.

It is, however, difficult to apply heat to an injured limb or other body part without severely restricting mobility of the patient. Various techniques have been and are used to provide heat, or the sensation thereof, in a portable fashion to permit mobility, including packs of heated fabrics and various rubefacients. However, their effects tend to be of very short duration since normal heat loss cools the hot packs quickly unless they are of burdensome volume and weight, and rubefacients tend to be either too strong at the outset or to have little effect after a brief interval.

Another approach which has been taken is the provision of a heating element enclosed within a fabric pad, or layers of pads, the element being heated by electrical current. The element and pad assembly is attached to a belt, band or strap arrangement having fasteners of conventional type so that it can be worn by the patient with the heating element adjacent the body area needing treatment. In order to make such a device portable, the current is supplied by a chemical battery, usually of the dry cell type, disposed in a pocket or otherwise carried on the body.

Recent advances in the power-delivering capabilities of batteries have made such devices more practical than before, but it remains true that these physically small power supplies have limited current-supplying capabilities over a limited interval of time, i.e., the current-time product is relatively small. Thus, prior art efforts to produce an efficient and effective portable therapeutic heating pad have not met with significant acceptance. Examples of prior art efforts in this general area are found in the following documents:

U.S. Pat. No. 2,178,397—Larkey
U.S. Pat. No. 3,016,446—Kalbach
U.S. Pat. No 3,178,559—Fogel et al
U.S. Pat. No. 3,292,628—Maxwell et al
U.S. Pat. No. 3,470,350—Lewis
U.S. Pat. No. 3,569,666—Murphy et al
Norwegian Pat. No. 109,776—Krosby

BRIEF DESCRIPTION OF THE INVENTION

An object of the present invention is to provide a portable therapeutic heating device which is small, compact and efficient and which maximizes the length of time during which heat is applied thereby to a body part.

A further object is to provide a heating device which distributes heat uniformly over the area covered by the device and which prevents the possibility of burning any portion of that area.

A still further object is to provide a heating device in which the heat source is a semiconductor device having a contact circuit which permits close control of the heat produced and, if desired, intermittent operation to extend battery life.

The apparatus disclosed herein can advantageously be used in the relief of pain arising from rib injuries, lumbar disc or vertabrae discomfort, shoulder or upper back conditions, thigh or knee problems, or tennis elbow, as examples.

Briefly described, the invention includes a portable therapeutic heating device for localized heating of a body part comprising the combination of first and second flexible electrically nonconductive sheets of substantially liquid impermeable material bonded to each other along their margins to form an envelope, an electrically nonconductive liquid contained in and substantially filling said envelope, a heat source comprising a semiconductor valve immersed in said liquid, bandage means attached to said envelope for holding said envelope in contiguous heat-transferring relationship with a selected portion of a body, a portable source of electrical energy, and control circuit means for interconnecting said source of energy and said valve, whereby said valve is energized by current passing therethrough from said source and the heat generated thereby is transferred to said liquid and to said selected portion of the body.

Advantageously, the structure also includes strips of nonconductive material extending in woven fashion through the envelope to retain the heating element in a desired location within the envelope, and the liquid contained therein is preferably silicone oil.

Figure 1:
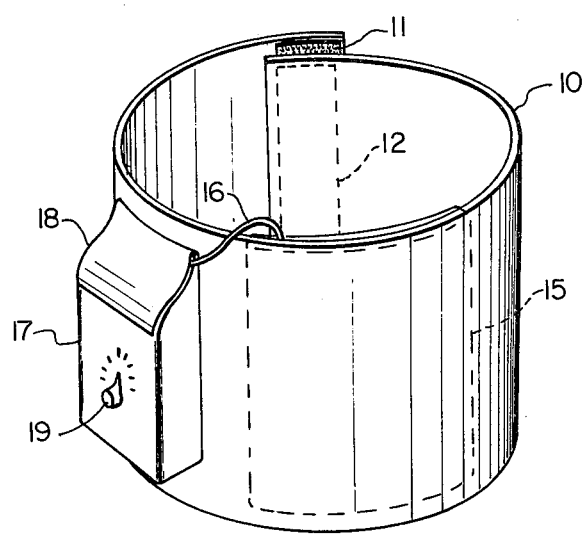
FIG. 1 is a schematic perspective view of a carrier for a heat applicator in accordance with the present invention.

To establish the general environment in which the present invention is used, there is illustrated in FIG. 1 a belt or bandage 10 which, in the specific form shown, is designed to encircle a body limb such as an arm or leg for application of heat to a portion thereof. The band is formed as an elongated strip having fastening means at the ends thereof. Conveniently, these can be snap fasteners or, as illustrated, mating strips 11 and 12 of hook-and-loop fastening material such as that commonly sold under the trademark VELCRO. At an intermediate position on the inner surface of belt 10 is a heat-producing structure 15, two embodiments of which are the subject of the present invention. The heat-producing device can be received in a pocket attached to the inner surface of belt 10, or, alternatively, it can be fixedly attached to the inner surface of the belt. An electrical conductor 16 is connected at one end to a heating element within device 15 and at the other end to a source of electrical energy which is illustrated in FIG. 1 as comprising batteries contained within a pocket 17 formed on the outer surface of band 10. The pocket 17 is provided with a flap 18 to permit replacement of the batteries, the flap being secured in place by suitable fasteners. A control element, such as a variable resistor controlled by an adjustment knob 19 can also be provided on the battery pocket.

It should be emphasized that the present invention does not rely upon the provision of a battery pocket on the applicator supporting band and, in numerous circumstances, it may be desirable to have the source of energy removed somewhat from the portion of the body being locally heated. Alternative arrangements will be readily recognized.

Figure 2:
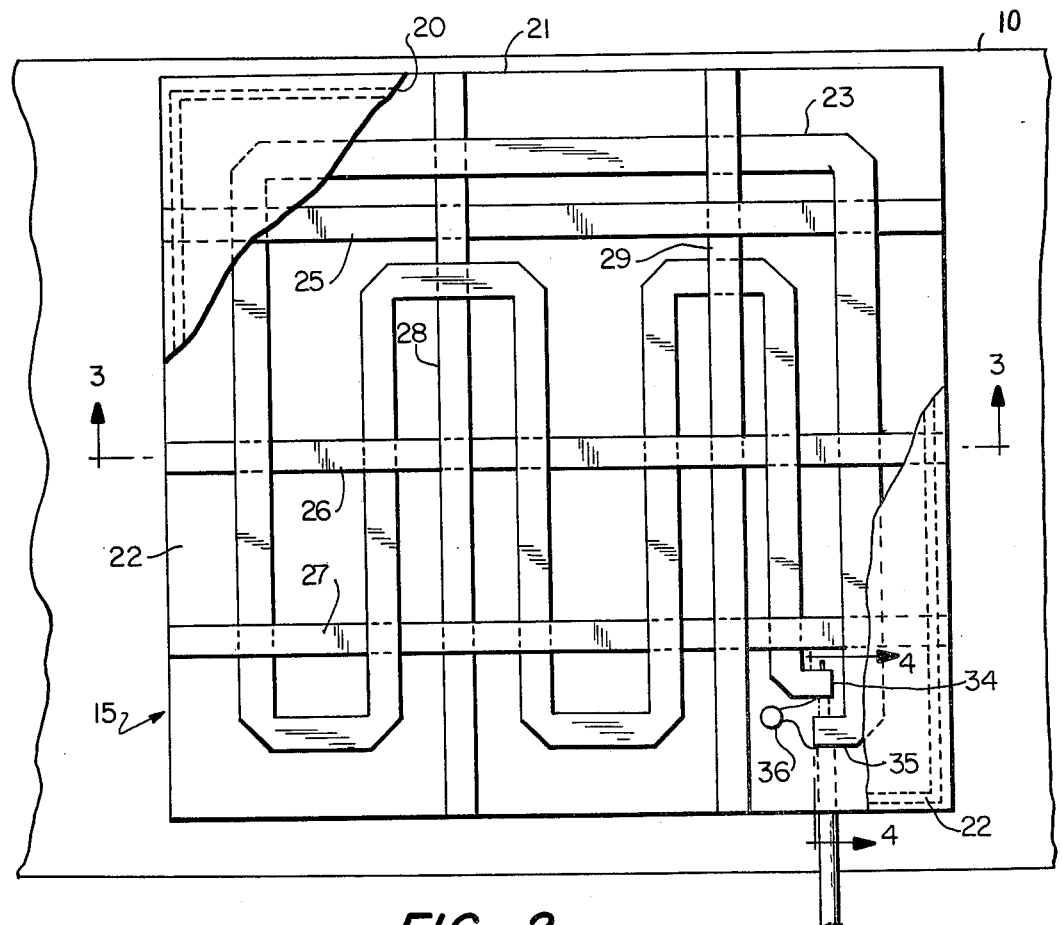
FIG. 2 is a plan view of a heat applicator in accordance with the invention.
Figure 3:
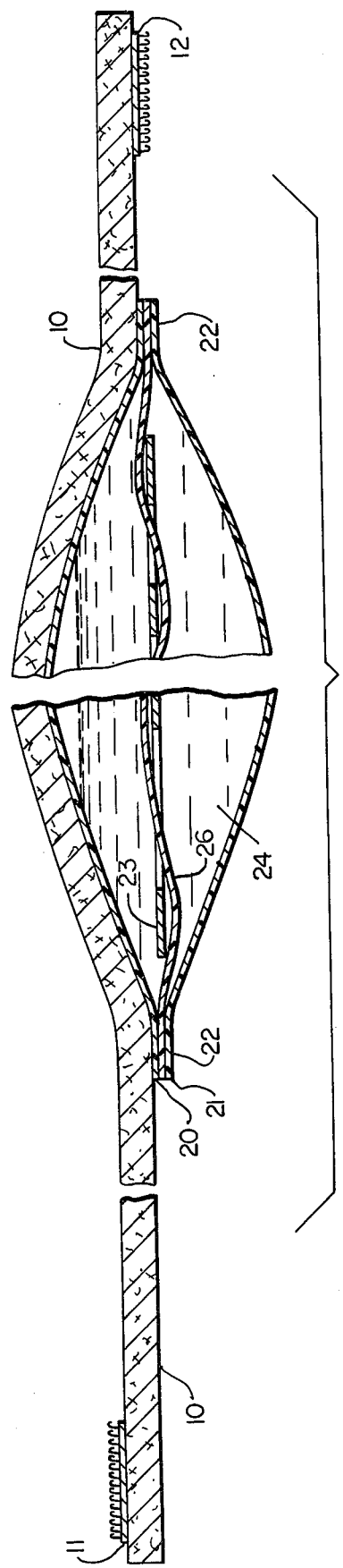
FIG. 3 is a transverse section along line 3—3 of FIG. 2.

Turning now to the first embodiment of the heating apparatus forming the present invention, there is shown in FIGS. 2 and 3 a plan and a sectional view of the device 15 itself, FIG. 3 being shown with the band attached and FIG. 2 being shown with the band omitted.

As seen in FIGS. 2 and 3, the structure includes first and second sheets of polymeric film 20 and 21, a major portion of sheet 20 being cut away in FIG. 2 to expose the heating element within. Sheets 20 and 21 are bonded to each other around the marginal edges thereof as by a radio frequency thermosealing process. The envelope thus formed can be generally square and, for example, can be between three and four inches long on each side.

The sheets forming the envelope are preferably formed from a plasticized, flexible, polymeric film having a high dielectric strength, good resistance to heat in the temperature range of interest, normally between about 95° F. (35° C.) to 160° F. (71° C.), and should be inert in the presence of silicone oil or other liquid selected for use therein. The film should, of course, also be heat-sealable, although other bonding techniques can be used. The film thickness is normally about 0.020 to 0.1 inches (0.5 to 2.5 mm.). Thus, a wide variety of films can be employed, including plasticized polyvinylchloride, plasticized vinylchloride-acetate copolymer, vinylidene cloride-vinylchloride copolymer, vinylnitrile rubber alloy, oriented polystyrene film, polymethylmethacrylate, or medium or high density polyethylene.

Within the envelope is a heating element 23 which is formed using a flat ribbon of resistance material which produces heat when electrical current is passed therethrough. The heating element is advantageously formed using a nichrome foil having a resistance of 3.76 ohms per foot, the foil being about 0.002 inches thick and 0.125 inches wide. For an envelope of the dimensions mentioned above, approximately 18 inches of foil can be folded in the pattern shown in FIG. 2 to form a generally sinuous heating element which occupies substantially the entire interior of the envelope, the outer portions thereof being inwardly spaced from the heat-sealed margins thereof. As shown, the foil can be folded so that legs thereof form a U-shaped portion around three outer sides of the envelope with the remainder following a sinuous path in the remainder of the envelope so that the two ends of the heating element are adjacent each other and near one corner of the envelope. This permits electrical conductors to be conveniently attached thereto.

The envelope also contains a quantity of an electrically nonconductive and inert fluid, such as silicone oil, the quantity thereof being sufficient to cause the sides of the envelope to bulge somewhat away from each other, permitting the heating element to be generally suspended within the fluid and spaced from the outer walls of the envelope. Again, using the dimensions mentioned above, approximately 12 cubic centimeters of fluid can be injected into the envelope. This can be accomplished after the margins thereof have been heat-sealed with the heating element therein by injecting the fluid using a hypodermic needle or the like at a marginal portion of the envelope, after which the opening formed by the needle is again heat-sealed shut.

In order to further enhance the positioning of the resistance element within the envelope, there is provided a plurality of locating strips 25, 26 and 27 extending parallel to each other and to two edges of the envelope, these strips being formed from a suitable material which can be the same as sheets 20 and 21. The ends of the strips can be bonded between the sheets forming the envelope by heat-sealing as the margins are formed. As will be observed most clearly in FIG. 3, the strips are woven in with the nichrome heating element section, in a manner analogous to weaving a basket, the lengths of the strips being chosen so that they remain relatively taut as the envelope is caused to bulge.

Additional strips 28 and 29 can also be provided running in a direction perpendicular to strips 25-27 to further enhance the positioning of the heating element.

Figure 4:
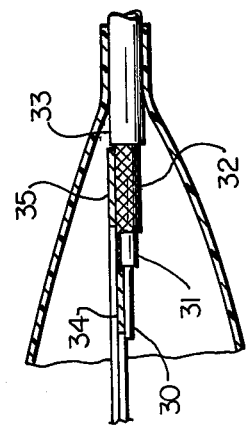
FIG. 4 is a partial sectional view along line 4—4 of FIG. 2.

As previously mentioned, the ends of the heating element are connected to electrical conductors which pass through the margin of the envelope, the connection thereof being more clearly shown in FIG. 4. As seen therein, a cable having a suitable conductor for this purpose is one having a central conductor 30 surrounded by a layer of insulation 31 which is, in turn, surrounded by a braided outer conductor 32, the braided conductor also being insulated as illustrated at 33. Teflon covered cable such as RG-188 can be used. A sufficient amount of central conductor 30 is exposed and soldered or welded to one end 34 of the heating element and a short portion of the braided outer conductor 32 is exposed to be connected, as by soldering, to the other end 35 of the heating element. A section of insulation 31 remains exposed to keep the two ends of the heating element apart. The other end of the conductors are connected to a suitable connector, of conventional type, for attachment to a battery or a plurality of series-connected batteries. In addition, a thermistor 36 can be connected between ends 34 and 35 to limit the temperature in the liquid 24 to a desired level such as, for example, 99° F.

The assembly thus far described can be put together by preassembling the folded nichrome foil with strips 25-29 woven through the foil. Ends 34 and 35 can be presoldered to the conductors, as described. This assembly is then placed on sheet 21 and sheet 22 is placed on top of the assembly and the margins of the sheets are sealed or bonded together. A hypodermic needle is then inserted through the seal between the sheets and silicone oil is injected therein, after which the injection opening is closed. The structure is then complete, except for attachment to band 10 which, as previously mentioned, can be by adhesion or by insertion into a pocket formed in the band.

As will be recognized, various forms of attachments can be used, depending upon the region of the body to which heat is to be locally applied.

Figure 6:
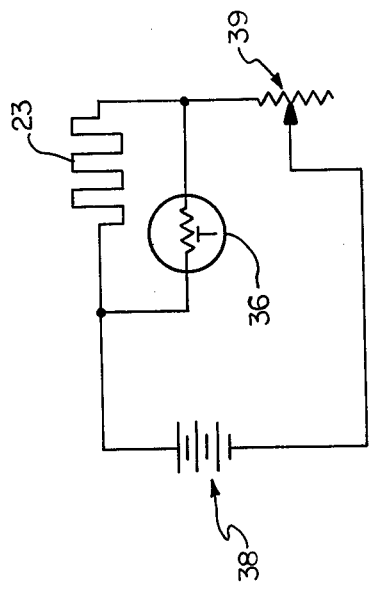
FIG. 6 is a schematic circuit diagram of a circuit usable with the embodiment of FIGS. 2-4.

FIG. 6 shows a very simple electrical schematic diagram illustrating heating element 23 with thermister 36 connected between the ends thereof. The heating element is connected in series circuit relationship with a battery 38 and can also be connected in series circuit relationship with a variable resistor or potentiometer 39, if desired, to permit control of the amount of current being delivered to the heating element. If control 39 is provided, thermistor 36 can be omitted.

Figure 5:
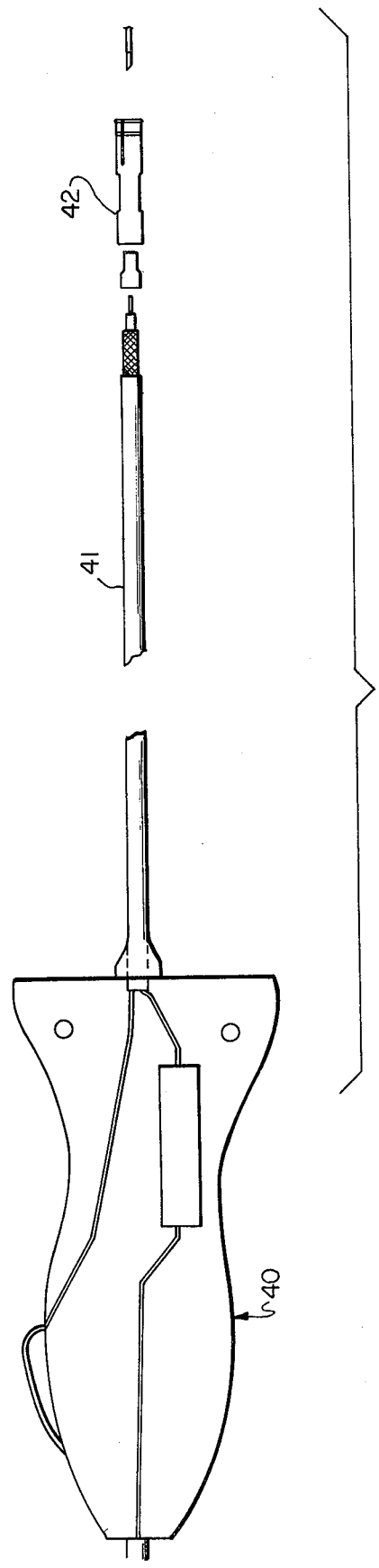
FIG. 5 is a schematic representation of an adaptor connector usable with the apparatus of FIGS. 2-4.

FIG. 5 illustrates an assembly usable to connect the heating element to an auxiliary source as a motor vehicle battery by insertion into the cigarette lighter receptacle commonly provided in such vehicles. For this purpose, a plug 40 is connected to a conductor 41, the plug 40 being shaped to enter the cigarette lighter receptacle. A suitable connector 42 is provided at the other end of the connector for attachment of the heating element which is provided with a suitable mating connector.

It will be recognized that the above-described structure, containing the liquid within the envelope and surrounding the heating element, greatly decreases the possibility of burning the body part in the event of the development of a "hot spot" in the heating element which might elevate a small portion thereof above the control point temperature. In addition, the fluid provides a medium for the storage of heat and greatly enhances the heat distribution throughout the localized area to be treated. The overall structure can be made relatively small in size and is therefore suitable for application of heat to small areas such as knees and elbows, or can be made of a greater size for treating larger areas such as back muscles.

A second embodiment of an apparatus in accordance with the invention is shown in FIGS. 7–10 wherein the means for converting electrical energy to heat is a semiconductive device such as a transistor. It has been found that it is possible to use a transistor or the like, connected to an appropriate control circuit, as the heat source when the transistor is immersed in a fluid such as silicone oil, with significant advantages. In this context, the term "transistor" will be used for brevity, but it will be recognized that other semiconductor valve devices could be employed if desired.

Figure 7:
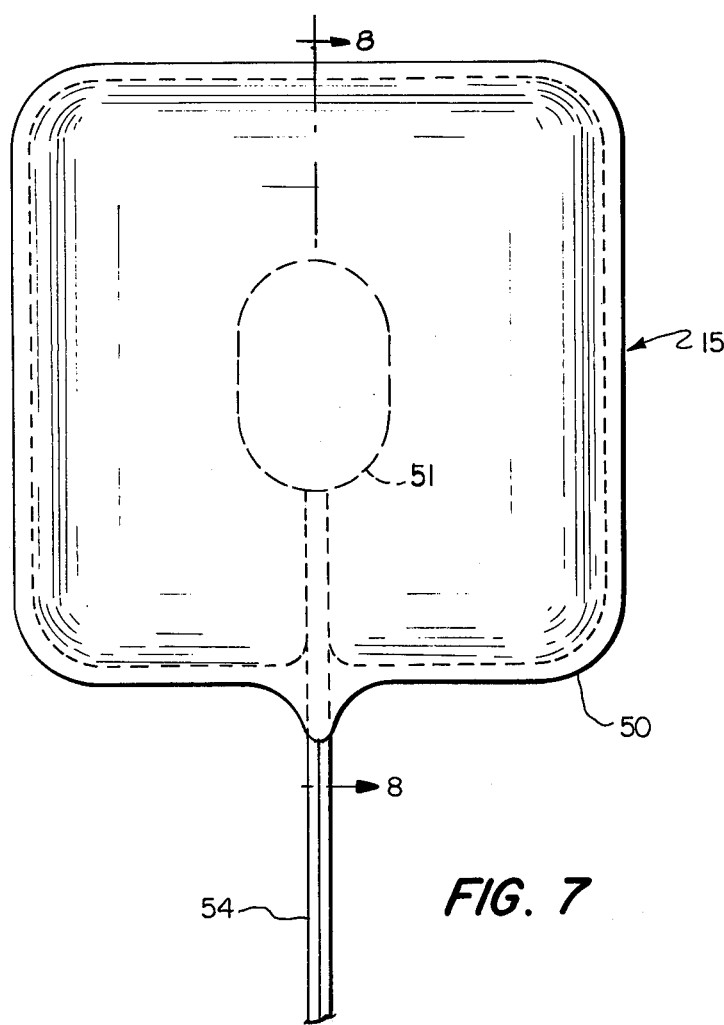
FIG. 7 is a plan view of a second embodiment of a heat applicator in accordance with the invention with the carrier omitted.
Figure 8:
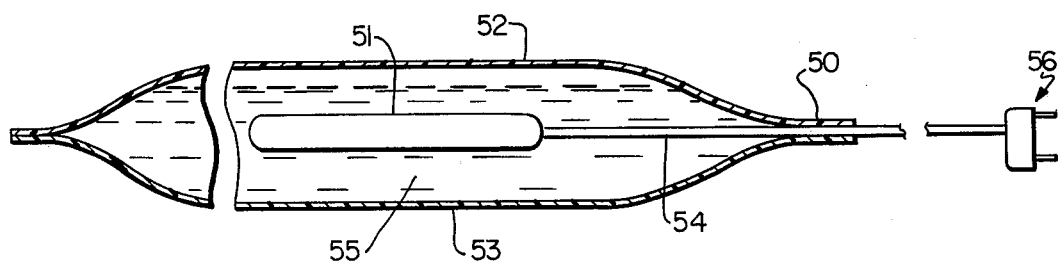
FIG. 8 is a partial side elevation of the device of FIG. 7 along line 8—8 thereof.

As shown in FIGS. 7 and 8, the heat-producing structure indicated generally at 15 includes an envelope 50 within which is disposed a transistor and control circuit 51 which can be encapsulated in a relatively thin layer of an electrically nonconductive material, not separately illustrated. Envelope 50 includes upper and lower sheets 52 and 53 of polymeric film which are similar in nature to sheets 20 and 21, FIG. 3. The margins of sheets 52 and 53 are bonded to each other, as described with reference to FIGS. 3 and 4, to form a fluid-tight envelope which is filled with a fluid 55 such as silicone oil, a suitable oil for this purpose being VS 12500 silicone oil manufactured by Dow Chemical Company. Electrical conductors, such as the wires in a 2-conductor ribbon cable 54, are connected to a heat producing circuit at conductors 62 and 65, respectively shown in FIG. 9. The cable extends out of the envelope between sheets 52 and 53 and can terminate in a suitable electrical convertor indicated generally at 56.

The characteristics of the film used for sheets 52 and 53 can be similar to that described in connection with the previous embodiment and will not be repeated.

Figure 9:
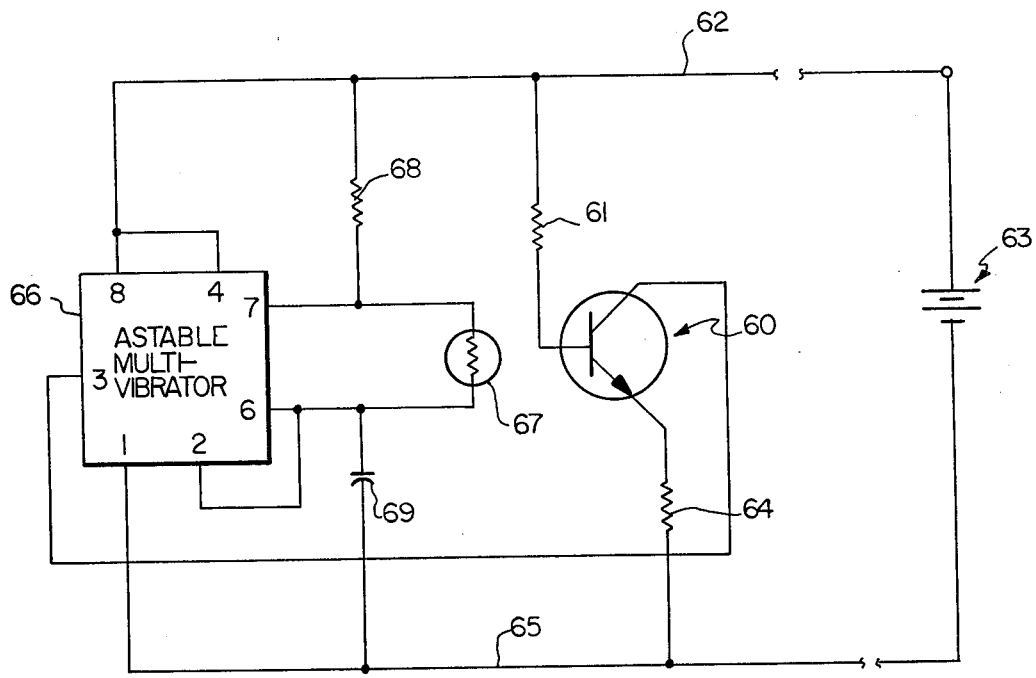
FIG. 9 is a schematic circuit diagram, partly in block form, of a control circuit usable with the embodiment of FIGS. 7 and 8.

A circuit usable as heat source 51 is shown in FIG. 9 and includes a conventional PNP transistor indicated generally at 60, the base electrode of which is connected through a biasing resistor 61 to a conductor 62 which is connected to the positive terminal of a DC voltage source, such as one or more batteries 63. The emitter electrode of the transistor is connected through a biasing resistor 64 to a conductor 65 which is connected to the negative terminal of the source. The collector of the transistor is connected to an output terminal 3 of an astable multivibrator 66 so that transistor 60 is rendered fully conductive during one-half of each cycle of the multivibrator. A temperture control for this device includes a temperature-sensitive resistor, such as a thermistor 67 which is connected across terminals 6 and 7 of the multivibrator. A resistor 68 and a capacitor 69 are connected between oposite ends of the thermistor and the positive and negative source terminals, respectively.

The terminal numbers given for the multivibrator are those for an integrated circuit identified as NE555, made by Signetics Corporation of Sunnyvale, California, which is one circuit suitable for this use, although other integrated or "wired" (discrete) circuits could be used. Substantially any PNP transistor of adequate power capacity is usable.

The circuit including thermistor 67, resistor 68 and capacitor 69 constitutes a temperature feedback timing curcuit to establish the pulse repetition rate of the multivibrator. The thermistor is chosen to have a positive temperature coefficient, i.e., increasing resistance with increasing temperature, so that as the temperature increases the pulse repetition rate decreases, toward a control point. The following are typical circuit values for use with a DC voltage source of 3–6 volts to reach a pulse rate of about 10 Hz. for the multivibrator and, therefore, for transistor 60.

resistor 68—0.9 megohms
resistor 61—1500 ohms
resistor 64—50 ohms
capacitor 69—0.1 microfarad The thermal feedback permits the frequency to vary ±4 Hz. around the 10 Hz. control point. With a battery source of two AA size dry cells, this system provides heat to the fluid, and to the body part being treated, at an average temperature of about 108° to 112° F. (42°–45° C.) for a period of from five to seven hours.

Figure 10:
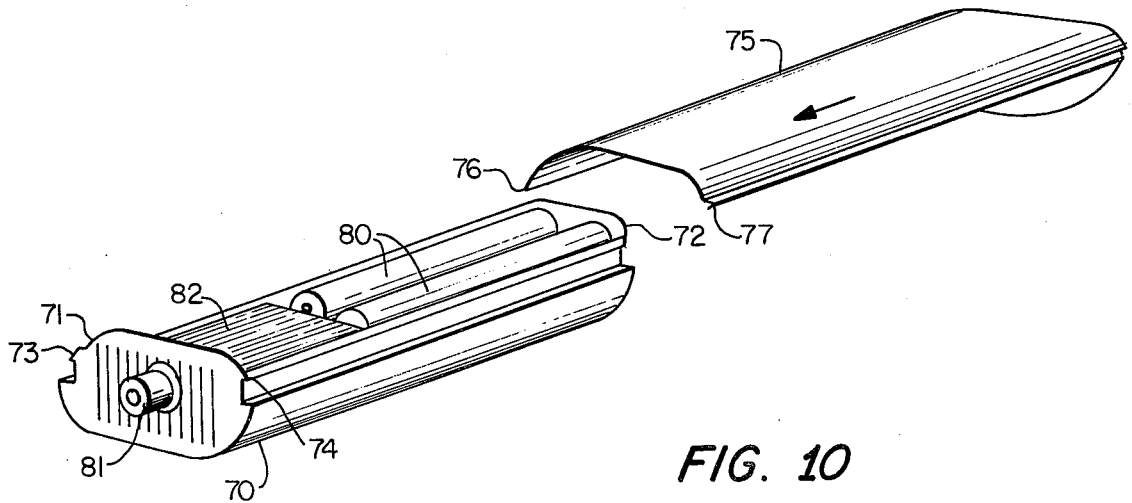
FIG. 10 is a perspective view of a module usable with the embodiment of FIGS. 7-9 to contain the power source and control circuits thereof.

A battery pack usable with this apparatus is shown in FIG. 10 and includes a housing 70 having an end wall 71. The sides ofthe housing are formed with inward grooves terminates in elongated lips 73 and 74. A cover 75 is shaped to conform to the upper open side of housing 70 and has indented edges 76 and 77 to engage lips 73 and 74, permitting the cover to slide onto the housing from the position shown in FIG. 10. Cover 75 has an end wall 78 which abuts the end of housing 70 opposite wall 71 when in its fully closed position.

The hollow interior of housing 70 is dimensioned to receive two or more batteries 80, which can be of the AA size. The housing also is provided with conventional contacts and supply voltage to a connector 81 mounted in wall 71.

Housing 70 can also be provided with a module 82 containing circuitry to permit recharging of batteries 80, if desired. The charging circuitry and details of the electrical aspects of the battery pack are not, in themselves, believed to be novel and are not described in detail.

While certain advantageous embodiments have been chosen to illustrate the invention, it will be understood by those skilled in the art that various changes and modifications can be made therein without departing from the scope of the invention as defined in the appended claims.

What is claimed is:

1. A portable therapeutic heating device for localized heating of a body part comprising the combination of
   first and second flexible thermally conductive and electrically nonconductive sheets of substantially liquid impermeable material bonded to each other along their margins to form a sealed envelope;
   a thermally conductive and electrically nonconductive liquid contained in and substantially filling said envelope;
   an electric heat source comprising a semiconductor electron valve immersed in said liquid;
   bandage means attached to said envelope for holding said envelope in contiguous heat-transferring relationship with a selected portion of a body;
   a portable source of electrical energy; and
   control circuit means for interconnecting said source of energy and said valve, whereby said valve is energizied by current from said source and the heat generated thereby is transferred to said liquid and to said selected portion of the body.

2. A device according to claim 1 wherein said valve is a transistor.

3. A device according to claim 2 wherein said control circuit means includes
   an astable multivibrator connected to said transistor to repetitively and periodically render said transistor conductive; and
   a timing circuit including a positive temperature coefficient resistance element connected to said multivibrator to control the repetition rate thereof, said resistance element being in heat transfer relationship with said fluid.

4. A device according to claim 3 wherein said fluid is silicone oil.

5. A portable therapeutic heating device for localized heating of an article comprising the combination of
   first and second flexible thermally conductive and electrically nonconductive sheets of substantially liquid impermeable material bonded to each other along their margins to form a sealed envelope;
   a thermally conductive and electrically nonconductive liquid contained in and substantially filling said envelope;
   an electric heat source comprising a semiconductor electron valve immersed in said liquid;
   means attached to said envelope for holding said envelope in contiguous heat-transferring relationship with a selected portion of an article; a portable source of electrical energy; and
   control circuit means for interconnecting said source of energy and said valve, whereby said valve is energized by current from said source and the heat generated thereby is transferred to said liquid and to said selected portion of the article.

* * * * *